(12) United States Patent
Oliveros Maita (10) Patent No.: US 12,138,470 B2
(45) Date of Patent: *Nov. 12, 2024

(54) MAGNETIC BIO-THERAPY DEVICE AND METHOD

(71) Applicant: SPSCANCO, LLC, Humble, TX (US)

(72) Inventor: Enios Rafael Oliveros Maita, Montgomery, TX (US)

(73) Assignee: SPScanco, LLC, Humble, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/325,402

(22) Filed: May 30, 2023

(65) Prior Publication Data

US 2024/0198123 A1    Jun. 20, 2024

Related U.S. Application Data

(63) Continuation of application No. 18/002,321, filed on Dec. 19, 2022, now Pat. No. 11,701,523.

(51) Int. Cl.
*A61N 2/06* (2006.01)
*H01F 7/02* (2006.01)

(52) U.S. Cl.
CPC ............... *A61N 2/06* (2013.01); *H01F 7/02* (2013.01)

(58) Field of Classification Search
CPC .. H01F 7/02; H01F 7/00; A61N 2/004; A61N 2/00; A61N 2/06
See application file for complete search history.

(56) References Cited

U.S. PATENT DOCUMENTS

| 9,999,380 B1 | 6/2018 | Demas |
| 11,701,523 B1* | 7/2023 | Rafael Oliveros Maita ................ A61N 2/06 600/15 |
| 2020/0108267 A1 | 4/2020 | Hunt |

OTHER PUBLICATIONS

"Design of Permanent Mul Tipole Magnets With Oriented Rare Earth Cobalt Material" to Halbach, K Publication date Aug. 1, 1979.

* cited by examiner

*Primary Examiner* — Samuel G Gilbert
(74) *Attorney, Agent, or Firm* — Matthew J Patterson (57) ABSTRACT

A magnetic bio-therapy device may include a ring having an inside diameter and an outside diameter and a bore defined by the inside diameter. In addition, the device may include a plurality of permanent magnets each having a magnetic field circumferentially spaced around the ring between the inside diameter and the outside diameter where each of the plurality of permanent magnets is oriented such that the magnetic field of each of the permanent magnets is directed in a predetermined direction.

28 Claims, 6 Drawing Sheets

Wherein the Halbach array comprises a magnetization pattern of any of k=2, k=3 and k=4
916

Wherein the is comprised of a first ring half and a second ring half, the method further comprising: coupling the first ring half and the second ring half; and slidably capturing the body part therebetween
918

*FIG. 9B*

MAGNETIC BIO-THERAPY DEVICE AND METHOD

CROSS REFERENCE TO RELATED APPLICATIONS

This application in a continuation of U.S. patent application Ser. No. 18/002,321 which application claims the benefit of U.S. Provisional Application Ser. No. 63/21,669,234 filed 30 Jun. 2021, as well as Patent Cooperation Treaty Patent Application Serial No. PCT/US22/73274 filed 30 Jun. 2022. The disclosure of the applications above are incorporated herein by reference in their entirety.

BACKGROUND OF THE DISCLOSURE

Field of the Disclosure

Embodiments of the disclosure generally relates to the field of bio-therapy, and more specifically, a device and methods for applying a magnetic therapy field to a patient that is not elsewhere provided for.

Description of the Related Art

There exists many apparatuses and methods in the prior art for magnetic therapy. Each of the apparatuses and methods of the prior art have deficiencies.

What is needed is a magnetic therapy device and method that cures the deficiencies of the prior art.

SUMMARY OF THE INVENTION

In one general aspect, magnetic bio-therapy device may include a ring having an inside diameter and an outside diameter and a bore defined by the inside diameter. A magnetic bio-therapy device may also include a plurality of permanent magnets each having a magnetic field circumferentially spaced around the ring between the inside diameter and the outside diameter where each of the plurality of permanent magnets is oriented such that the magnetic field of each of the permanent magnets is directed in a predetermined direction.

Implementations may include one or more of the following features. A magnetic bio-therapy device where the predetermined direction forms a Halbach array. A magnetic bio-therapy device where the plurality of permanent magnets circumferentially spaced around the ring form the Halbach array having a magnetization pattern of any of k=2, k=3 and k=4. A magnetic bio-therapy device where the Halbach array is of a type K=2 and is configured to produce a planar magnetic field is in accordance with the following:

$$H = M_r \ln\left(\frac{R_o}{R_i}\right) y$$

wherein $M_r$ is a ferromagnetic remanence, $R_i$ is the inside diameter and $R_o$ is the outside diameter and a direction of the planar magnetic field is y. A magnetic bio-therapy device where the ring is configured to be positioned around a part of a body at a predetermined angle and is further configured to induce the planar magnetic field in the part of the body. A magnetic bio-therapy device where the ring may include a first ring half and a second ring half and where the first ring half and the second ring half are configured to be positioned over the part of the body and removably coupled together joining the first ring half and the second ring half slidably capturing the part of the body therebetween. A magnetic bio-therapy device may include a fixation device configured to removably fix the ring to the part of the body. A magnetic bio-therapy device where the ring may include a cylinder having a length where the plurality of permanent magnets are circumferentially spaced around the ring and linearly positioned along the length of the cylinder. A magnetic bio-therapy device where the plurality of permanent magnets are circumferentially spaced around the ring in a plurality of concentric rows.

In one general aspect, a method may include providing a ring having an inside diameter and an outside diameter and a bore defined by the inside diameter. A method may also include positioning a plurality of permanent magnets each having a magnetic field circumferentially spaced around the ring between the inside diameter and the outside diameter. A method may furthermore include orienting each of the plurality of permanent magnets such that the magnetic field of each of the permanent magnets is directed in a predetermined direction. A method may in addition include producing a planar magnetic field within the bore. A method may moreover include positioning a body part within the bore. A method may also include applying the planar magnetic field to the body part.

Implementations may include one or more of the following features. A method where orienting each of the plurality of permanent magnets forms a Halbach array. A method where the Halbach array may include a magnetization pattern of any of k=2, k=3 and k=4. A method may include forming the magnetization pattern K=2 Halbach array and producing the planar magnetic field is in accordance with the following:

$$H = M_r \ln\left(\frac{R_o}{R_i}\right) y$$

wherein $M_r$ is a ferromagnetic remanence, $R_i$ is the inside diameter and $R_o$ is the outside diameter and a direction of the planar magnetic field is y. A method where the positioning step may include positioning the ring at a predetermined angle the body part. A method where the ring may include a first ring half and a second ring half, the method may include coupling the first ring half and the second ring half; and slidably capturing the body part therebetween. A method may include removably fixing the ring to the body part. A method where the ring may include a cylinder having a length, the method having positioning the plurality of permanent magnets linearly along the length of the cylinder. A method may include positioning the plurality of permanent magnets in a plurality of concentric rows.

In one general aspect, a device may include provide a ring having an inside diameter and an outside diameter and a bore defined by the inside diameter. A device may also include position a plurality of permanent magnets each having a magnetic field circumferentially spaced around the ring between the inside diameter and the outside diameter. A device may furthermore include orient each of the plurality of permanent magnets such that the magnetic field of each of the permanent magnets is directed in a predetermined direction. A device may in addition include produce a planar magnetic field within the bore. A device may moreover include position a body part within the bore. A device may also include apply the planar magnetic field to the body part.

Implementations may include one or more of the following features. A device where orienting each of the plurality of permanent magnets forms a Halbach array. A device where the Halbach array may include a magnetization pattern of any of k=2, k=3 and k=4. A device may include: forming the magnetization pattern K=2 Halbach; and producing the planar magnetic field is in accordance with the following:

$$H = M_r \ln\left(\frac{R_o}{R_i}\right) y$$

wherein $M_r$ is a ferromagnetic remanence, $R_i$ is the inside diameter and $R_o$ is the outside diameter and a direction of the planar magnetic field is y. A device where the positioning step may include positioning the ring at a predetermined angle to the body part. A device where the ring is may include of a first ring half and a second ring half, the method may include coupling the first ring half and the second ring half and slidably capturing the body part therebetween. A device may include removably fixing the ring to the body part. A device where the ring may include a cylinder having a length, the method including positioning the plurality of permanent magnets linearly along the length of the cylinder. A device may include positioning the plurality of permanent magnets in a plurality of concentric rows.

Implementations may include one or more of the following features. The magnetic bio-therapy device where the magnetic bio-therapy device may include a Halbach array. The Halbach array is of magnetization pattern of type k=2 and the planar magnetic field is in accordance with the following:

$$H = M_r \ln\left(\frac{R_o}{R_i}\right) y$$

wherein $M_r$ is a ferromagnetic remanence, $R_i$ is the inside diameter and $R_o$ is the outside diameter and a direction of the planar magnetic field is y The ring is configured to be positioned around a part of a body at a predetermined angle and is further configured to induce the planar magnetic field in the part of the body. The ring may include a first ring half and a second ring half and where the first ring half and the second ring half are configured to be positioned over the part of the body and removably coupled together joining the first ring half and the second ring half slidably capturing the part of the body therebetween. The magnetic bio-therapy device may include a fixation device configured to removably fix the ring to the part of the body. The fixation device is an inflatable generally cylindrical bag.

BRIEF DESCRIPTION OF THE DRAWINGS

So that the manner in which the above-recited features of the present disclosure can be understood in detail, a more particular description of the disclosure, briefly summarized above, can be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

In the following detailed description of the embodiments, reference is made to the accompanying drawings, which form a part hereof, and within which are shown by way of illustration specific embodiments by which the examples described herein can be practiced. It is to be understood that other embodiments can be utilized, and structural changes can be made without departing from the scope of the disclosure. For instance, as part of the present disclosure, examples will be given in terms of All of the methods disclosed and claimed herein can be made and executed without undue experimentation in light of the present disclosure. While the apparatus and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the disclosure.

Although the invention(s) is/are described herein with reference to specific embodiments, various modifications and changes can be made without departing from the scope of the present invention(s), as presently set forth in the claims below. Accordingly, the specification and figures are to be regarded in an illustrative rather than a restrictive sense, and all such modifications are intended to be included within the scope of the present invention(s). Any benefits, advantages, or solutions to problems that are described herein with regard to specific embodiments are not intended to be construed as a critical, required, or essential feature or element of any or all the claims.

Figure 1:
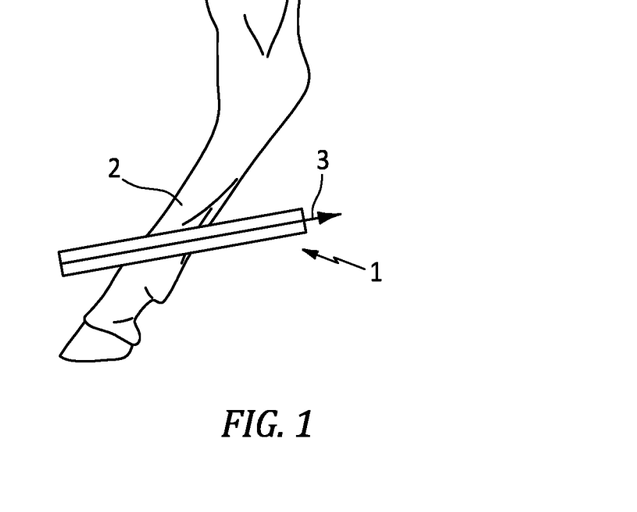
FIG. 1 is a side view of a magnetic bio-therapy device in accordance with the present disclosure.

Referring first to FIG. 1, there is shown is an illustration that will be used to illustrate the application and operation principals of a magnetic bio-therapy device 1 of the present disclosure. Magnetic bio-therapy device 1 is shown as applied to a leg 2 of a patient, in this particular embodiment the patient is a horse. It should be appreciated by those skilled in the art that although this embodiment is described with regard to a particular animal, the embodiments of magnetic bio-therapy device 1 of the present disclosure apply to other types of living creatures including, but not limited to humans. As will be described in more detail herein below, magnetic bio-therapy device 1 produces a dipolar magnetic field 3 within the tissue of the patient having a circular cross section in the direction of the arrow. The magnetic field is inventively produced within the tissue of a patient in the plane of magnetic bio-therapy device 1 as will disclosed in more detail herein after. Magnetic field 3 is uniformly produced in the tissue of the patient. In certain embodiments of the present disclosure magnetic bio-therapy device 1 is held stationary and in other embodiments the magnetic bio-therapy device is translated along the body part being treated such as leg 2.

Figure 2:
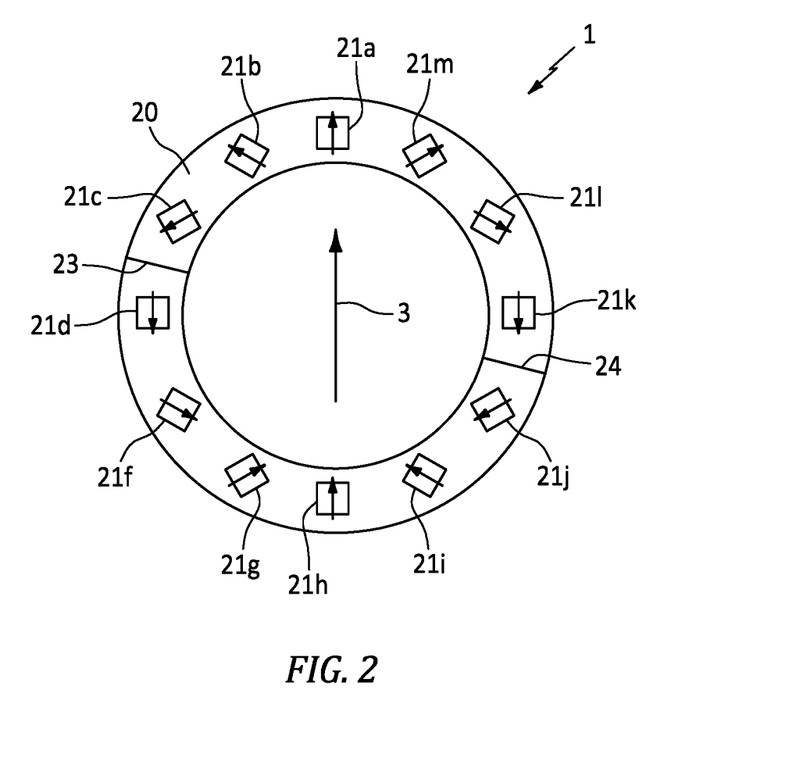
FIG. 2 is a conceptual diagram of the magnetic fields produced by a magnetic bio-therapy device accordance with the present disclosure.

Referring now to FIG. 2, there is shown magnetic bio-therapy device 1 in more detail comprising ring 20 and magnets 21a-21m arranged evenly spaced around midpoint circumference of the ring between its inside diameter and outside diameter. The magnets 21a-21m can comprise any type of permanent magnet or electromagnetic magnets. The direction of the magnetic field for each of the magnets 21a-21m is indicated by the arrow for each of the respective magnets. Although the embodiment in FIG. 2 comprises 12 magnets 21a-21m, embodiments with more or fewer magnets are contemplated to be within the scope of the present disclosure. Ring 20 is comprised of a non-ferromagnetic material and which material can include plastics, aluminum, some stainless steels and the like. It should be appreciated by those skilled in the art that ring 20 can comprise other shapes, such as elliptical, depending on the shape of the magnetic field desired and the portion of a patient to be treated. In addition, a plurality of rings 20 can be used and which plurality of rings can be oriented at predetermined angle relative to the leg 2 (FIG. 1) or at differing predetermined angles. Ring 20 further includes pockets formed or machined therein to receive magnets 21a-21m therein and the magnets may be affixed therein using any known techniques. In some embodiments, magnets 21a-21m are press fit into ring 20 and can be affixed using an appropriate adhesive. In some embodiments of the present disclosure, magnets 21a-21m are approximately 0.5 inch cubes and are comprised of neodymium type of magnet although other sizes and types of magnets are within the scope the present disclosure. It should be appreciated by those skilled in the art that the size and type of the magnets affect the size and strength of the magnetic field produced by magnetic bio-therapy device 1. For instance, larger magnets can be used to produce a larger magnetic field for larger portions of a patient's body. The increase in the size and/or width of the magnets can increase the width of the magnetic field produced. In the embodiment shown, magnets 21a-21m produce a combined magnetic field in the plane of ring 20 and in the direction of arrow 3. It should be appreciated by those skilled in the art that magnetic bio-therapy device 1 resembles a Halbach array of the type k=2. For the special case of an Halbach array wherein k=2, the magnetic field inside the bore is uniform and is given by $$H = M_r \ln\left(\frac{R_o}{R_i}\right) \hat{y}$$ (Equation 1)

where $M_r$ is the ferromagnetic remanence, and the inner and outer radii of ring 20 are $R_i$ and $R_o$ respectively. The magnetic field H is in the y direction (direction of arrow 2). In certain embodiments for portions of a patient's body having a diameter between 2 inches and 4 inches $R_i$ can be approximately 6 inches and $R_o$ can be approximately 8 inches. Ring 20 further includes split lines 23, 24 splitting the ring into a first half and a second half which allow the ring to be opened such that magnetic bio-therapy device 1 can be installed over a portion of a patient to be treated even if that portion has no free end such as a neck or a torso. The split ring can include alignment features, hinges and closure devices as are known in the art (not shown).

In an example embodiment, has an inner radius $R_i$=2.88 inches and an outer radius $R_o$=4.13 inches and a thickness of 1.00 inches. Magnets 21a-21m are approximately 0.5 inch cubes and are comprised of neodymium type. The magnetic field H was measure within the bore using a Vernier Magnetic Field Sensor that measures a vector component of the magnetic field near the sensor tip. The tip can be adjusted, allowing the user to measure fields that are parallel or perpendicular to the long axis of the sensor. The sensor uses a Hall-effect transducer. It produces a voltage that is linear with magnetic field. The sensor measures the component of the magnetic field that is perpendicular to a spot on the end of the sensor tip. The reading is positive when the spot on the sensor points toward a magnetic south pole. In this way Equation 1 was validated for both the strength of the magnetic field as well as the direction of the magnetic field.

Although magnetic bio-therapy device 1 is shown having a circular cross section forming a cylinder, other shapes are contemplated by the present disclosure. For example, an embodiment of magnetic bio-therapy device includes an elliptical shape wherein the eclipse is comprised of a major radius and a minor radius for purposes of Equation 1. Such embodiments can be useful in therapy applications applied to different body parts such as on a wrist of a person to treat carpal tunnel syndrome. The elliptical shape would better follow the wrist. Other shapes and applications are contemplated by the present disclosure.

Figure 3:
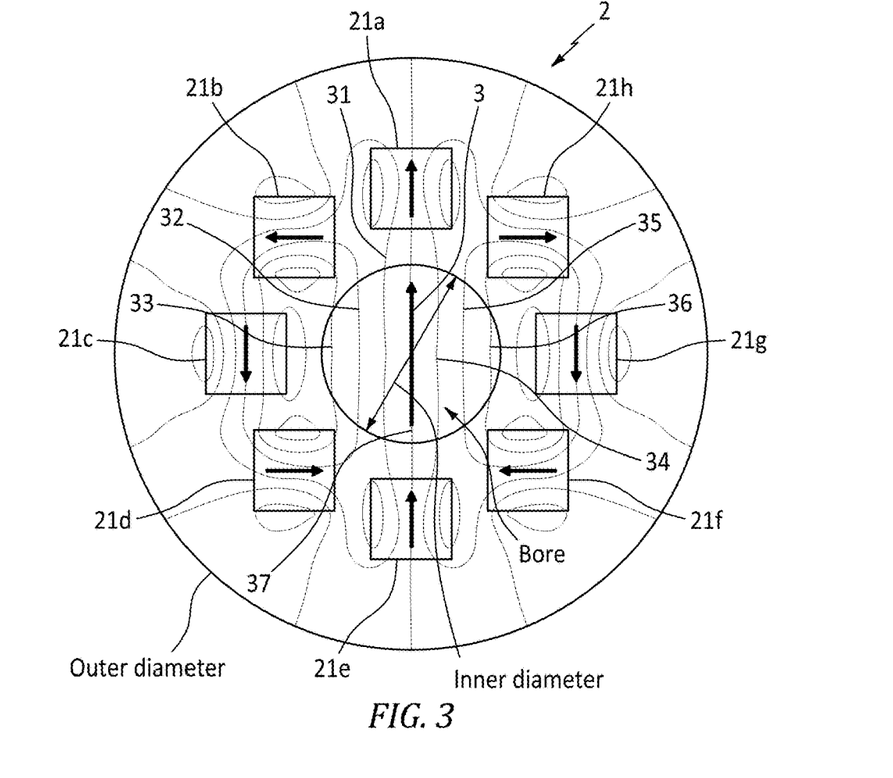
FIG. 3 is a diagrammatic view of the combined magnetic field of a magnetic bio-therapy device in accordance with the present disclosure.

The magnetic fields produced by the individual magnets and the combined magnetic effect can best be visualized with reference to FIG. 3. The embodiment shown includes 8 magnets 21a-21h and the direction of the magnetic field for each of the magnets is indicated by the arrow for each of the respective magnets. It can be seen that magnets 21a-21e produce a combined magnetic field 31 and that magnets 21b-21d produced combined magnetic fields 32, 33. Magnets 21a-21e produce a combined magnetic field 31 and that magnets 21b-21d produced combined magnetic fields 32, 33. Similarly, magnets 21a and 21e-21h produce a combined magnetic field 34 and that magnets 21f-21h produced combined magnetic fields 35, 36. Further magnets 21a, 21e produce combined magnetic field 37. Because of the orientation of magnets 21a-21h, the combined magnetic fields 31-37 produce a total combined planar (with respect to the plane of ring 20) magnetic field in the direction of arrow 3.

Figure 4:
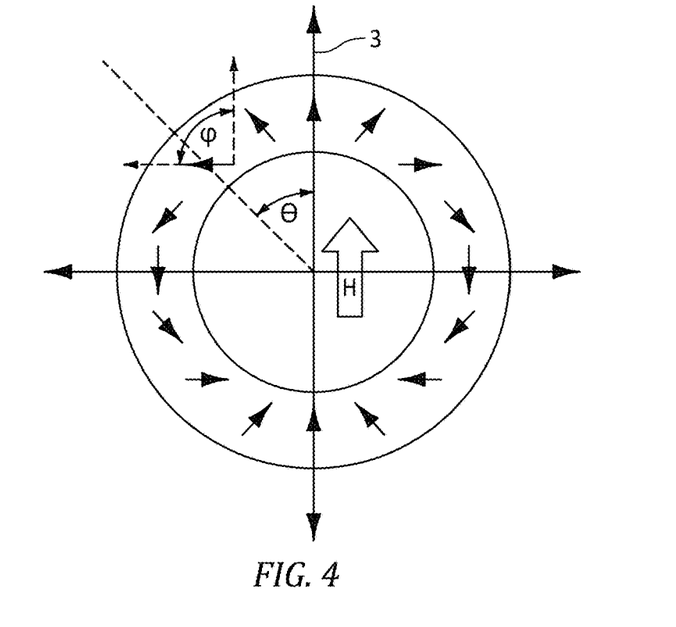
FIG. 4 is a schematic of the individual magnetic fields and the magnetic field H for a magnetic bio-therapy device in accordance with the present disclosure.

Referring to FIG. 4, there is shown a schematic of the individual magnetic fields and the magnetic field H (Equation 1) for a magnetic bio-therapy device of the present disclosure having 18 permanent magnets positioned around the ring. The magnetic polarization orientation, φ, varies as 2 times the azimuthal angle, θ, wherein:

$$\varphi = 2\theta \quad \text{(Equation 2)}$$

and $$\theta = 360/n \quad \text{(Equation 3)}$$

wherein n is the number of magnets. This relationship holds for the orientation of magnets regardless of the number of magnets in any particular embodiment of a magnetic bio-therapy device of the present disclosure. This orientation mimics the fringe field that would result from a perfect magnetic dipole placed at the center of the ring. Because the individual magnets mimic this dipolar magnetization pattern, the result is a planar and bipolar magnetic field in the direction of arrow 3.

Figure 5:
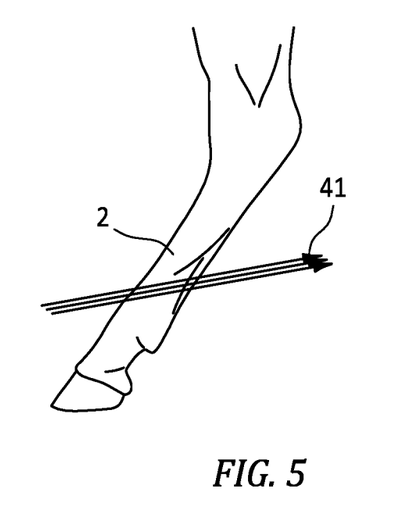
FIG. 5 is an illustration of the magnetic field produced by a magnetic bio-therapy device in accordance with the present disclosure.

Referring to FIG. 5, there is shown a schematic representation of combined planar magnetic fields 41 produced by magnetic bio-therapy device 1 in the direction of the arrows through leg 2. It should be appreciated by those skilled in the art that the combined planar magnetic fields 41 produced by magnetic bio-therapy device 1 is useful in producing therapeutic benefits not hereto for seen in the industry.

Figure 6:
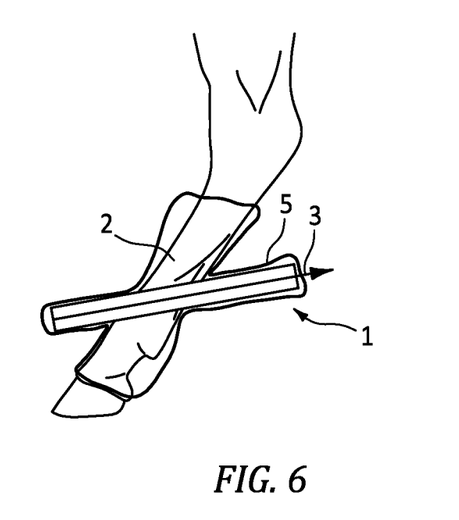
FIG. 6 is a side view of a magnetic bio-therapy device and installation unit in accordance with the present disclosure.

Referring to FIG. 6, there is shown magnetic bio-therapy device 1 positioned on leg 2 and held in place by air bag 5. Air bag 5 is shown as translucent and comprises a customized air splint configured to accommodate magnetic bio-therapy device 1 and snugly conform to leg 2. Air bag 5 is generally cylindrical such that magnetic bio-therapy device 1 can be inserted into the air bag and slid over leg 2. In operation, the portion of a patient to be treated by magnetic bio-therapy device 1 is selected and the appropriately sized magnetic bio-therapy device and air bag 5 selected. Although the embodiments are shown as applied to the leg 2 of a horse the magnetic bio-therapy device 1 of the present disclosure is not so limited. The magnetic bio-therapy device 1 of the present disclosure can be applied to animal and humans alike in areas including arms, necks, wrists, torsos, feet, legs, knees, shoulders and the like. Other methods of applying magnetic bio-therapy device 1 are contemplated by the present disclosure including sleeve that includes hook and loop fasteners, elastic bandages and other known devices. It is further contemplated by the present disclosure that magnetic bio-therapy device 1 can be positioned near a body part, such as a knee or elbow, wherein the body part is partially or wholly disposed within the inside diameter of ring 20.

Figure 7:
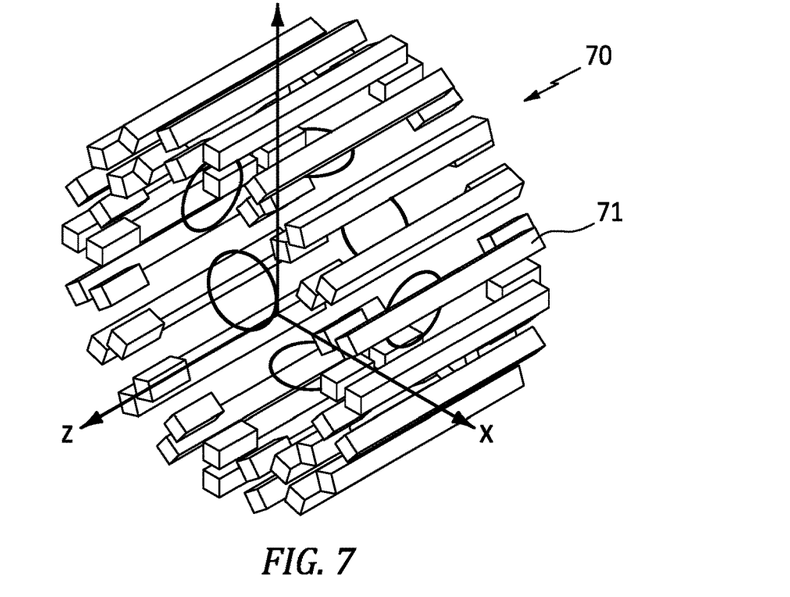
FIG. 7 is a 3-dimensional schematic view of a magnetic bio-therapy device in accordance with the present disclosure.
Figure 8:
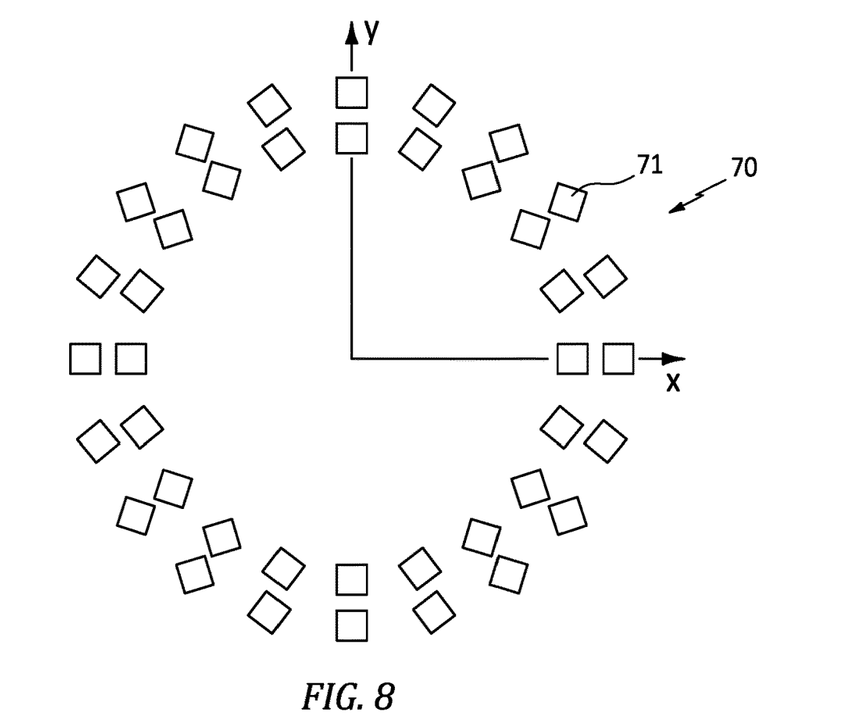
FIG. 8 is a schematic frontal view of magnetic bio-therapy device in accordance with the present disclosure.

Referring now to FIG. 7, there is show a 3-dimensional view of a magnetic bio-therapy device 70 in accordance with the present disclosure that comprises a cylinder having an appreciable length in the Z direction. The cylinder is comprised of individual magnets that when stacked together make up a bar of magnets of which 71 is an example. All of the other bars are of the same make up. It will be appreciated by those skilled in the art that magnetic bio-therapy device 70 will produce a significantly higher magnetic field than a cylinder comprising a fewer number of magnets positioned in the Z direction. The combined the magnetic field H (Equation 1) is in the Y direction. Referring to FIG. 8, there is shown a schematic frontal view of magnetic bio-therapy device 70 showing the concentric rows of the outer arrangement of bars and the inner arrangement of bars. The polarity of the magnetic orientation of the outer arrangement of bars and the inner arrangement of bars differs because of the different number of magnets and the diameters upon which they arranged in accordance with Equations 2 and 3.

Figure 9A:
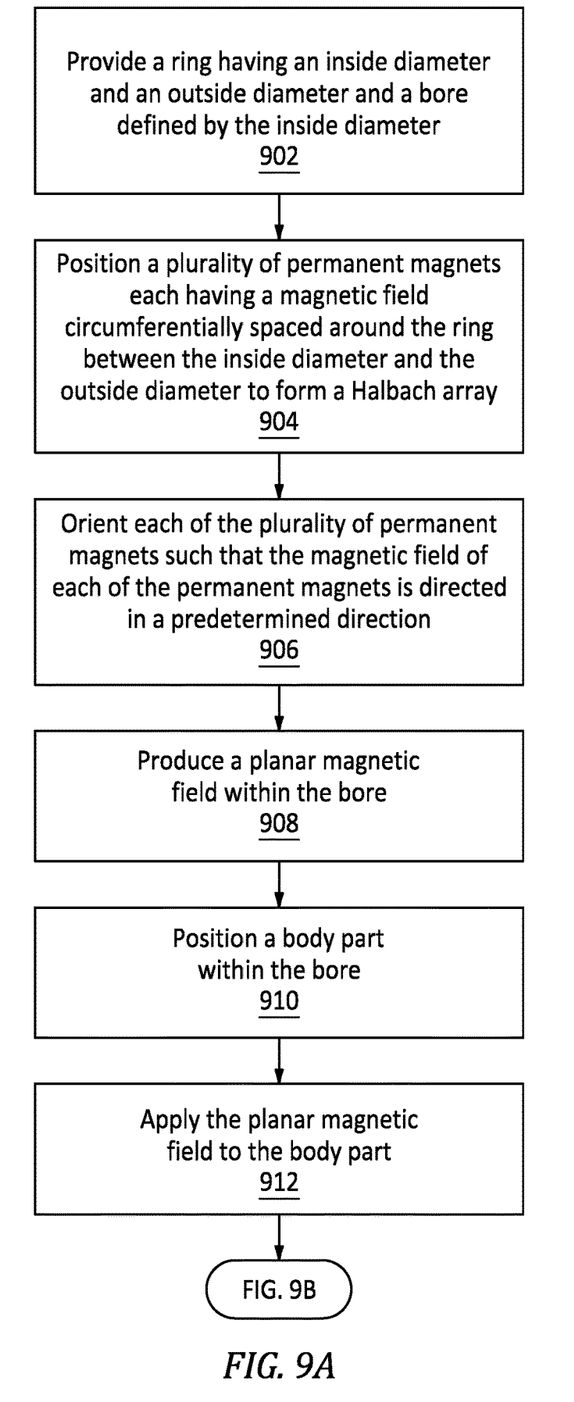
FIG. 9A is a flowchart of an example process 900 of applying magnetic therapy using a magnetic bio-therapy device in accordance with the present disclosure.
Figure 9B:
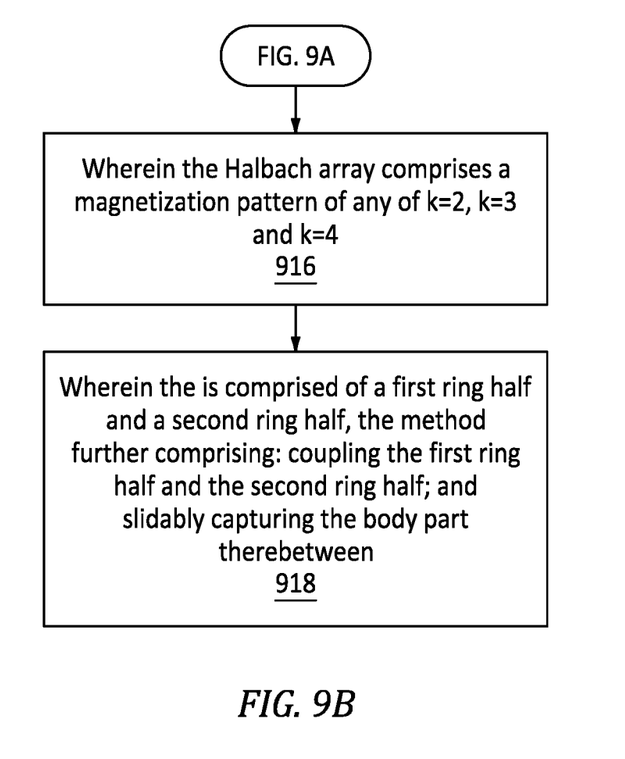
FIG. 9B is a continuation of the flowchart of FIG. 9A of an example process 900 of applying magnetic therapy using a magnetic bio-therapy device in accordance with the present disclosure.

FIG. 9A-B is a flowchart of an example process 900. In some implementations, one or more process blocks of FIG. 9A-B may be performed by a device. As shown in FIG. 9A-B, process 900 may include providing a ring having an inside diameter and an outside diameter and a bore defined by the inside diameter (block 902). For example, the device may provide a ring having an inside diameter and an outside diameter and a bore defined by the inside diameter, as described above. As also shown in FIG. 9A-B, process 900 may include positioning a plurality of permanent magnets each having a magnetic field circumferentially spaced around the ring between the inside diameter and the outside diameter (block 904). For example, the device may position a plurality of permanent magnets each having a magnetic field circumferentially spaced around the ring between the inside diameter and the outside diameter, as described above. As further shown in FIG. 9A-B, process 900 may include orienting each of the plurality of permanent magnets such that the magnetic field of each of the permanent magnets is directed in a predetermined direction forming a Halbach array (block 906). For example, the device may orient each of the plurality of permanent magnets such that the magnetic field of each of the permanent magnets is directed in a predetermined direction, as described above. As also shown in FIG. 9A-B, process 900 may include producing a planar magnetic field within the bore (block 908). For example, the device may produce a planar magnetic field within the bore, as described above. As further shown in FIG. 9A-B, process 900 may include positioning a body part within the bore (block 910). For example, the device may position a body part within the bore, as described above. As also shown in FIG. 9A-B, process 900 may include applying the planar magnetic field to the body part (block 912). For example, the device may apply the planar magnetic field to the body part, as described above.

Process 900 may include additional implementations, such as any single implementation or any combination of implementations described below and/or in connection with one or more other processes described elsewhere herein.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms "a" and "an" are defined as one or more unless stated otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements.

While the foregoing is directed to embodiments of the present disclosure, other and further embodiments of the disclosure may be devised without departing from the basic scope thereof, and the scope thereof is determined by the claims that follow.

The invention claimed is:

1. A magnetic bio-therapy device, comprising:
a ring having an inside diameter and an outside diameter and a bore defined by the inside diameter; and a plurality of permanent magnets each having a magnetic field circumferentially spaced around the ring between the inside diameter and the outside diameter wherein each of the plurality of permanent magnets is oriented such that the magnetic field of each of the permanent magnets is directed in a predetermined direction to produce a plurality of magnetic fields in a single magnetic field direction within the bore and traversing across the bore in the plane of the ring.

2. The magnetic bio-therapy device of claim 1 wherein the predetermined direction forms a Halbach array.

3. The magnetic bio-therapy device of claim 2 wherein the plurality of permanent magnets circumferentially spaced around the ring form the Halbach array wherein a magnetization pattern is k=2.

4. The magnetic bio-therapy device of claim 3 wherein the Halbach array is of a type K=2 and is configured to produce the plurality of magnetic fields in accordance with the following:

$$H = M\_r [\ln(-) [ R\_o/R\_i ]] y$$

wherein $M_r$ is a ferromagnetic remanence, $R_i$ is the inside diameter and $R_o$ is the outside diameter and the single magnetic field direction of the plurality of magnetic fields is y.

5. The magnetic bio-therapy device of claim 4 wherein the ring is configured to be positioned around a part of a body at a predetermined angle and is further configured to induce the plurality of magnetic fields in the part of the body.

6. The magnetic bio-therapy device of claim 5 wherein the ring is comprised of a first ring half and a second ring half and wherein the first ring half and the second ring half are configured to be positioned over the part of the body and removably coupled together joining the first ring half and the second ring half slidably capturing the part of the body therebetween.

7. The magnetic bio-therapy device of claim 5 further comprising a fixation device configured to removably fix the ring to the part of the body.

8. The magnetic bio-therapy device of claim 7 wherein the fixation device is an inflatable generally cylindrical bag.

9. The magnetic bio-therapy device of claim 2 wherein the ring comprises a cylinder having a length wherein the plurality of permanent magnets are circumferentially spaced around the ring and linearly positioned along the length of the cylinder.

10. The magnetic bio-therapy device of claim 9 wherein the plurality of permanent magnets are circumferentially spaced around the ring in a plurality of concentric rows.

11. A method of applying magnetic therapy comprising:
providing a ring having an inside diameter and an outside diameter and a bore defined by the inside diameter;
positioning a plurality of permanent magnets each having a magnetic field circumferentially spaced around the ring between the inside diameter and the outside diameter;
orienting each of the plurality of permanent magnets such that the magnetic field of each of the permanent magnets is directed in a predetermined direction;
producing a plurality of magnetic fields within the bore forming a single magnetic field direction traversing the bore of the ring;
positioning a body part within the bore; and
applying the plurality of magnetic fields to the body part in the single magnetic field direction.

12. The method of applying magnetic therapy of claim 11 wherein orienting each of the plurality of permanent magnets forms a Halbach array.

13. The method of applying magnetic therapy of claim 12 wherein the Halbach array comprises a magnetization pattern of k=2.

14. The method of applying magnetic therapy of claim 13 further comprising:
forming the magnetization pattern K=2; and
producing the plurality of magnetic fields in accordance with the following:

$$H = M\_r [\ln(-) [ R\_o/R\_i ]] y$$

wherein $M_r$ is a ferromagnetic remanence, $R_i$ is the inside diameter and $R_o$ is the outside diameter and the single magnetic field direction of the plurality of magnetic fields is y.

15. The method of applying magnetic therapy of claim 12 wherein the positioning a body part within the bore comprises positioning the ring at a predetermined angle to the body part.

16. The method of applying magnetic therapy of claim 12 wherein the ring is comprised of a first ring half and a second ring half, the method further comprising:
coupling the first ring half and the second ring half; and
slidably capturing the body part therebetween.

17. The method of applying magnetic therapy of claim 16 further comprising removably fixing the ring to the body part.

18. The method of applying magnetic therapy of claim 12 wherein the ring comprises a cylinder having a length, the method comprising positioning the plurality of permanent magnets linearly along the length of the cylinder.

19. The method of applying magnetic therapy of claim 18 further comprising positioning the plurality of permanent magnets in a plurality of concentric rows.

20. A device for applying magnetic therapy comprising:
a ring having an inside diameter and an outside diameter and a bore defined by the inside diameter;
a plurality of permanent magnets each having a magnetic field circumferentially spaced around the ring between the inside diameter and the outside diameter;
each of the plurality of permanent magnets oriented such that the magnetic field of each of the permanent magnets is directed in a predetermined direction to form a single magnetic field direction within the bore and traversing the inside diameter of the ring to produce a plurality of magnetic fields within the bore in the single magnetic field direction;
wherein the ring is configured to position a body part within the bore; and
the device is configured to apply the plurality of magnetic fields to the body part in the magnetic field direction.

21. The device of claim 20, wherein each of the plurality of permanent magnets are oriented to form a Halbach array.

22. The device of claim 21, wherein the Halbach array comprises a magnetization pattern of k=2.

23. The device of claim 22, wherein the device is configured to:
form the magnetization pattern K=2; and
produce the plurality of magnetic fields in accordance with the following:

$$H = M\_r [\ln(-) [ R\_o/R\_i ]] y$$

wherein Mr is a ferromagnetic remanence, Ri is the inside diameter and Ro is the outside diameter and the single magnetic field direction of the plurality of magnetic fields is y.

24. The device of claim 21, wherein the ring is configured to be positioned at a predetermined angle to the body part.

25. The device of claim 21, wherein the ring is comprised of a first ring half and a second ring half, the device further configured to:
   couple the first ring half and the second ring half; and
   slidably capturing the body part therebetween.

26. The device of claim 25, further configured to removably fix the ring to the body part.

27. The device of claim 21, wherein the ring comprises a cylinder having a length, the device comprising the plurality of permanent magnets positioned linearly along the length of the cylinder.

28. The device of claim 27, further comprising the plurality of permanent magnets positioned in a plurality of concentric rows.

\* \* \* \* \*